United States Patent
Peene et al.

(10) Patent No.: US 9,075,068 B2
(45) Date of Patent: Jul. 7, 2015

(54) INTEGRATED PARTICLE TRAP FOR CAPILLARY PLOT COLUMNS

(75) Inventors: Jan Adriaan Peene, Middelburg (NL); Liying Yu, Folsom, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 127 days.

(21) Appl. No.: 13/601,008

(22) Filed: Aug. 31, 2012

(65) Prior Publication Data

US 2014/0060331 A1    Mar. 6, 2014

(51) Int. Cl.
| | |
|---|---|
| *G01N 30/60* | (2006.01) |
| *G01N 30/56* | (2006.01) |
| *G01N 30/00* | (2006.01) |
| *B01D 15/22* | (2006.01) |
| *B01D 15/20* | (2006.01) |

(52) U.S. Cl.
CPC ......... *G01N 30/6078* (2013.01); *Y10T 29/4998* (2015.01); *G01N 2030/567* (2013.01); *G01N 30/6004* (2013.01); *G01N 2030/6008* (2013.01); *G01N 2030/484* (2013.01); *B01D 15/22* (2013.01); *G01N 2030/6013* (2013.01); *B01D 15/206* (2013.01)

(58) Field of Classification Search
CPC ................ G01N 30/482; G01N 30/56; G01N 2030/484; G01N 2030/562; G01N 2030/565; G01N 2030/567; G01N 30/6004; G01N 30/603; G01N 30/6078; G01N 2030/6008; G01N 2030/6013
USPC ....................... 96/101; 95/88; 73/23.35, 23.39
See application file for complete search history.

(56) References Cited

U.S. PATENT DOCUMENTS

| | | |
|---|---|---|
| 4,793,920 A | 12/1988 | Cortes et al. |
| 5,288,310 A | 2/1994 | Peters et al. |
| 5,599,445 A | 2/1997 | Betz et al. |
| 5,607,580 A | 3/1997 | Betz et al. |
| 5,609,756 A | 3/1997 | Betz et al. |
| 5,620,603 A | 4/1997 | Betz et al. |
| 5,630,937 A | 5/1997 | Betz et al. |

OTHER PUBLICATIONS

Ronald E. Majors and Jaap de Zeeuw, "The Development and Applications of PLOT Columns in Gas-Solid Chromatography", Chromatography Online, Oct. 1, 2010.*
Marsman et al., "On-Line Single Column Capillary Gas Chromatographic Analysis of All Reactants and Products in the Synthesis of Fuel Methanol from Hydrogen and Oxides of Carbon", Journal of High Resolution Chromatography, vol. 16, pp. 141-145, Mar. 1993.*
de Zeeuw et al., "PoraPLOT Q: A Porous Layer Open Tubular col. Coated with Styrene-Divinylbenzene Copolymer", Journal of High Resolution Chromatography & Chromatography Communications, vol. 11, pp. 162-167, Feb. 1988.*
EP 13176807.9-1554, Extended European Search Report, Oct. 28, 2013.
CN 201320463345.1, First Notification for Correction, Mar. 6, 2014.
L. Blomberg, J. Chromatogr. 115: 365 (1975).

* cited by examiner

*Primary Examiner* — Robert Clemente

(57) ABSTRACT

A porous layer open tubular (PLOT) column includes capillary tubing; one or two particle traps disposed inside one or two end sections of the capillary tubing; and a stationary phase comprising a porous or non-porous material coated inside a main section of the capillary tubing. A method for preparing a porous layer open tubular (PLOT) column includes preparing one or two particle traps inside one or two end sections of a capillary tubing; and preparing a stationary phase comprising a layer of a porous material coated inside a main section of the capillary.

18 Claims, 8 Drawing Sheets

INTEGRATED PARTICLE TRAP FOR CAPILLARY PLOT COLUMNS

BACKGROUND OF INVENTION

1. Field of the Invention

The present invention relates to porous layer open tubular (PLOT) columns for gas chromatography.

2. Background Art

Porous layer open tubular (PLOT) columns are useful for the analysis of volatile compounds. A PLOT column typically comprises a capillary column having a layer of a porous material coated on the inside surface of the columns. A PLOT column may contain a different type of coated materials to provide unique selectivity, allowing for the separation of gaseous compounds at room temperature. The retention times of compounds in PLOT columns depends partly on diffusion of the compounds into the thin porous layer and partly on the interaction between the compounds with the solid surfaces. Generally, gases and light hydrocarbons can be resolved at room temperature. In addition, PLOT columns can be heated to higher temperatures to elute higher boiling compounds.

The coatings of PLOT columns may contain various porous and non-porous materials, including alumina (aluminum oxide), molecular sieves, carbon based materials, and porous organic and inorganic polymers. PLOT columns are typically coated using a suspension of the porous material (e.g., colloidal alumina or polymer suspensions). The suspension medium is then removed leaving behind a stable uniform layer. Alternatively, the porous layer may be formed by polymerization in-situ. This layer of alumina or polymers may be further modified with various additives to give different selectivity.

A traditional PLOT column typically contains a layer of particles of 5-50 μm thick adhered to the inside tubing walls. The layers of porous materials are fragile due to the presence of particles and high porosity. The particles may come out of the column during use, especially when the tube is mechanically stressed or fast temperature changes take place. These particles dislodged from the columns may cause various problems. For example, detectors contaminated with particles typically generate electronic noise, which shows up as spikes in the baseline of the chromatogram. In extreme cases, detector flow can be obstructed by particle buildup. Particles can also affect valves by becoming lodged in the valve and causing leaks or restricting flow.

A possible solution for this problem can be an integrated porous plug as described in U.S. Pat. No 4,793,920. In principal this will work, because the porous plug will catch all the particles. However, another problem should occur, because all the particles will cumulate on one point, on the porous plug. This will clog the porous plug and will give a high pressure drop.

To alleviate these problems, PLOT columns may contain bonded stationary phases to provide higher mechanical and thermal stability. For example, U.S. Pat. Nos. 5,599,445, 5,607,580, 5,609,756, 5,620,603, and 5,630,937, all issued to Betz et al., disclose columns coated with a composition comprising a siloxane polymer having carbon bodies bonded thereto by direct carbon-to-silicon bonds. The columns are contacted with a mixture of the bodies and a hydrosiloxane polymer. The mixture is heated to cause the polymer to be bonded to the nucleophilic bodies, typically by C—Si, C—O—Si, Si—O—Si or Si—O—Al bonds, and to the column by reaction with the surface silanol or other nucleophilic groups.

Another example of a bonded stationary phase to provide a higher mechanical stability is the PoraBOND Q column (Chrompack/Varian). The coating of these columns is made in-situ to obtain a more homogeneous layer.

Even though the bonded particle approach minimizes the problems with particle leaks, it may not completely alleviate problems due to thermal expansion, which may cause the particles to break from the wall. An alternative approach is to use a particle trap. A particle trap is typically a piece of fused silica tubing coated with a reagent that can catch the released particles. Reagents that may be used in particle traps include siloxanes, which function as "glue" to bind particles dislodged from the PLOT columns.

The particle traps are typically coupled to the ends of PLOT columns by compression fits. These connector-particle trap configurations have two shortcomings: (i) the trap is typically coupled with a glass press fit connector, which may leak; and (ii) any particles dislodged from the column may be trapped at the connector, leading to clogging of the connector and a high pressure drop. Therefore, there remains a need for a better solution.

SUMMARY OF INVENTION

One aspect of the invention relates to porous layer open tubular (PLOT) columns. A PLOT column in accordance with one embodiment of the invention includes a capillary tubing; one or two particle traps disposed inside one or two end sections of the capillary tubing; and a stationary phase comprising a porous or non-porous material coated inside a main section of the capillary tubing. The capillary tubing may be a glass or metal capillary. The particle traps may comprise a product of a siloxane, a polysiloxane, a polyethyleneglycol or polypropyleneglycol. The porous or non-porous material in the stationary phase may comprise a polymer, which may be a divinylbenzene polymer or a styrene-divinylbenzene copolymer.

Another aspect of the invention relates to methods for preparing porous layer open tubular (PLOT) columns. A method in accordance with one embodiment of the invention includes preparing one or two particle traps inside one or two end sections of a capillary tubing; and preparing a stationary phase comprising a layer of a porous material coated inside a main section of the capillary. The capillary tubing may be a glass capillary. The method may further include deactivating the glass capillary, which is performed prior to the preparing of one or two particle traps.

In accordance with some embodiments of the invention, the step of preparing one or two particle traps is performed prior to the step of preparing the stationary phase. In accordance with some embodiments of the invention, the step of preparing one or two particle traps is performed after the step of preparing the stationary phase. In accordance with some embodiments of the invention, preparing one or two particle traps and preparing the stationary phase are performed simultaneously (e.g., in a single step).

Another aspect of the invention relates to methods for preparing a porous layer open tubular (PLOT) column having at least one particle trap. A method in accordance with one embodiment of the invention includes the steps of stripping a first section of a stationary phase coating from a first end of a PLOT column and preparing a first particle trap in the stripped first section. In some embodiments of the invention, the method further includes the steps of stripping a second section of the stationary phase coating from a second end of the PLOT column; and preparing a second particle trap in the stripped second section. In some embodiments of the invention, the method further includes the steps of preparing the particle traps directly over the PLOT coating.

Other aspects and advantages of the invention will be apparent from the following description and the appended claims.

DEFINITION

As used herein, the term "capillary tubing" refers to a tubing forming a PLOT column. The tubing may be a metal or glass (fused silica) capillary. A PLOT column contains capillary tubing and a coating of porous or non-porous material on the inside of the capillary tubing to form a stationary phase. In accordance with embodiments of the invention, a PLOT column will include one or two particle traps at one or both "end sections" of the capillary tubing, while the stationary phase is in the "main section" of the capillary tubing.

The term "main section" refers to the section having the stationary phase. Thus, if only one end has a particle trap, then the main section may include all remaining section of the tubing, including the other end section that does not have particle trap. The term "end section" refers to the section at one end of the capillary tubing for accommodating the particle trap.

As used herein, the term "stationary phase" refers to the coating of a porous material in a PLOT column. When an analyte is carried by a mobile phase (i.e., carrier gas) through a PLOT column, the analyte may partition between the porous layer (stationary phase) and the carrier gas (mobile phase) to result in separation of different components.

As used herein, the term "particle trap" refers to coatings in an end region of a PLOT column for capturing particles. The particle traps may be at one or both ends of a PLOT column. If only at one end, it would be at the outlet end of the column, to protect the detector.

DETAILED DESCRIPTION

Embodiments of the invention relate to PLOT capillary columns having integral particle traps. A PLOT capillary column with an integrated particle trap does not need any connector to connect the particle traps to the column. Therefore, there is no danger that the connectors and the particle traps may cause leakage or blockage.

Figure 1:
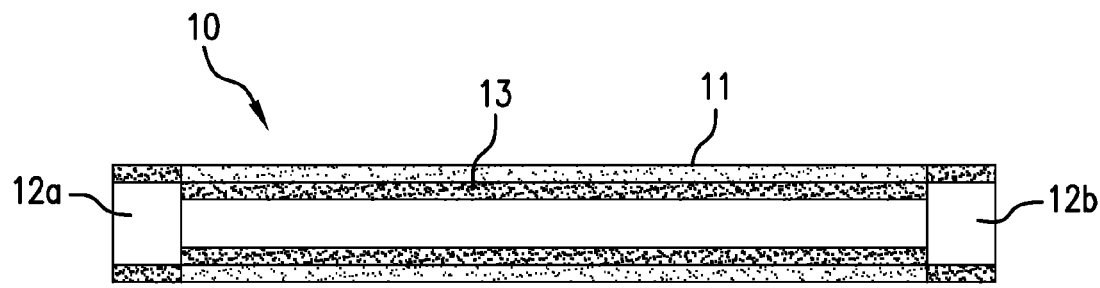
FIG. 1 shows a diagram illustrating a PLOT column having particle traps in accordance with one embodiment of the invention.

FIG. 1 shows a schematic illustrating a PLOT column having integral traps in accordance with embodiments of the invention. A PLOT column of the invention may be similar to a conventional PLOT column in its construction, dimension, or materials. For example, a PLOT column of the invention may comprise a capillary tubing, which may be a metal tubing or glass capillary tubing. Preferred embodiments of the invention may have glass capillary tubing. PLOT columns of the invention may have an inside diameter from about 0.1 mm to about 1.0 mm, such as about 0.2 mm, about 0.32 mm, and about 0.53 mm. The lengths of PLOT columns of the invention may be from about 5 m to about 100 m, preferably from about 10 m to about 60 m, such as about 10 m, about 20 m, about 30 m, about 40 m, about 50 m, and about 60 m. Please note that any numerical range given in this description is intended to include any numbers between the limits, as if these numbers are individually disclosed.

As shown in FIG. 1, the PLOT column 10 has a main section 11 having a stationary phase 13 (a layer of a porous material) coated on the inside of the column. At both ends of the column 10, there are particle traps 12a and 12b. The entire column, including the main section 11 and the two end sections (particle traps 12a ad 12b), are made with a single capillary tubing (capillary column). In other words, the particle traps 12a and 12b and the main section 11 form an integral unit, without any connectors.

As noted above, a typical PLOT column may have a length of several meters to several tens of meters (e.g., 10 m, 15 m, 20 m, 30 m, 40 m, 50 m, or 60 m). The particle traps may be made to a selected length regardless of the overall PLOT column length. Alternatively, the particle traps may be made to an appropriate length depending on the overall length of the column. In accordance with embodiments of the invention, the particle traps (or particle trap regions) may have any suitable length, for example from about 0.1 m to about 10 m, preferably from about 0.5 m to about 5 m, more preferably from about 1 m to about 3 m. The film thickness of the particle trap may have any suitable value, for example about 0.1 to about 10 micron, preferably from about 0.2 to about 1 micron.

The materials for use in the particle traps may be any materials known in the art. The function of a particle trap is to catch any particles dislodged from the column. Thus, any material that can capture or glue the dislodged particles may be used. Examples of suitable materials include silicon compounds (e.g., organosilicon compounds or polysiloxanes), or waxes. Examples of polysiloxanes may include polydimethylsiloxane, dimethylsiloxane methylvinylsiloxane, or a mixture thereof. Examples of waxes are polyethyleneglycol or polypropyleneglycol.

The materials for the stationary phases of PLOT columns of the invention may be any materials known in the art. Common PLOT columns may have stationary phases made of alumina, molecular sieve, carbon, or porous polymers. The following examples will use PLOT columns having porous polymers to illustrate embodiments of the invention. However, these particular examples are for illustration only. One skilled in the art would appreciate that embodiments of the invention may include other types of stationary phases. Among the porous polymers for use in stationary phases in PLOT columns, the common polymers may include divinylbenzene polymer or styrene-divinylbenzene copolymer.

Visual description of a column with integrated particle traps: One can easily observe the integrated particle traps in glass columns. The PLOT layers have a different color than the particle traps. Colors of the PLOT layer are light yellow to dark brown or green, but not transparent. The integrated particle traps are also light yellow to dark brown, but always transparent. This visual description does not apply when the particle traps coating is applied over the PLOT layer. For this particular embodiment the color of the particle trap section and the PLOT column section will be similar.

In accordance with embodiments of the invention, PLOT columns having integral particle traps may be prepared by several methods. For example, one may make the particle traps first and then make the stationary phase in the capillary column. Alternatively, one may make the stationary phase first in the capillary column, and then make the particle traps. Alternatively, one may make both the stationary phase and the particle traps in one step. Finally, one can make particle traps coated over the PLOT phase.

Figure 2:
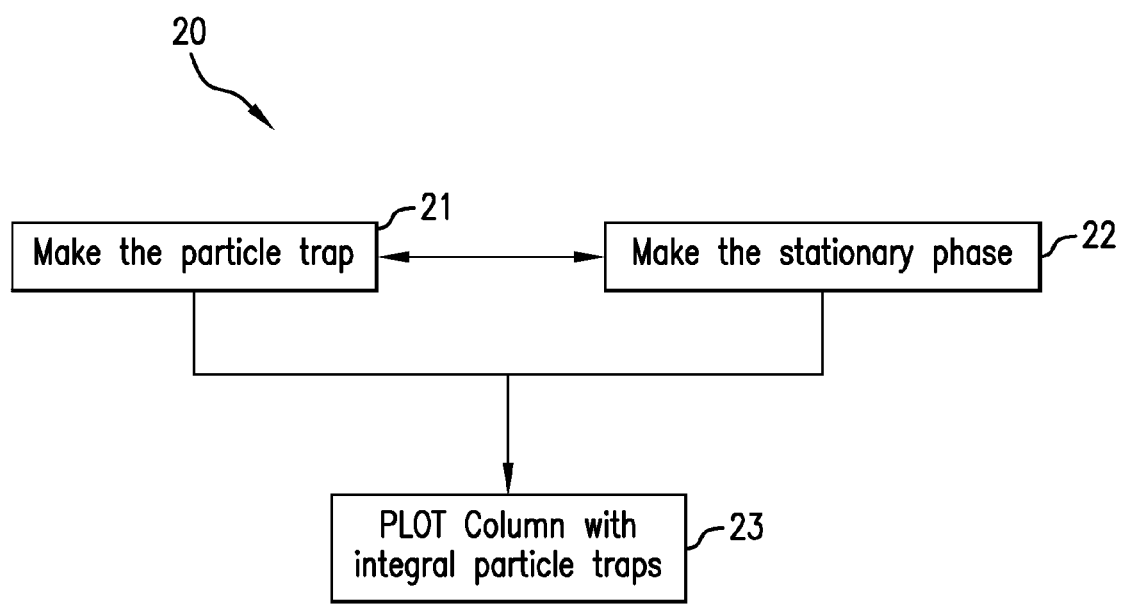
FIG. 2 shows a diagram illustrating methods for making a PLOT column having particle traps in accordance with one embodiment of the invention.

FIG. 2 shows a diagram summarizing the steps in these methods. A method 20 in accordance with embodiment of the invention may include a step 21 of making the particle traps (e.g., 12a and 12b in FIG. 1) and a step 22 of making the stationary phase (e.g., 13 in FIG. 1) to produce a PLOT column with integral particle traps 23. The particle traps may be made with any materials known in the art (e.g., polysiloxanes) for capturing particles that may be dislodged from the columns. The stationary phase may use any materials known in the art for PLOT columns. For example, the stationary phase may be made of divinylbenzene polymers or styrene-divinylbenzene copolymers.

In accordance with embodiments of the invention, the two steps 21 and 22 shown in FIG. 2 may be performed in series in either order (i.e., step 21 followed by step 22, or step 22 followed by step 21), or these steps 21 and 22 may be performed simultaneously (i.e., in a single step).

These methods may be better illustrated with specific examples. The following examples use PLOT columns (particularly, Q-type PLOT columns) to illustrate methods of the invention. However, one skilled in the art would appreciate that the uses of PLOT Q columns are for illustration only, and that these methods may also be used with other types of columns. Many Q-type PLOT columns are commercially available. Examples of PLOT columns include, PoraPLOT Q, PoraBOND Q, HP-PLOT Q, and GS-Q. These columns are available from Agilent Technologies.

Figure 3:
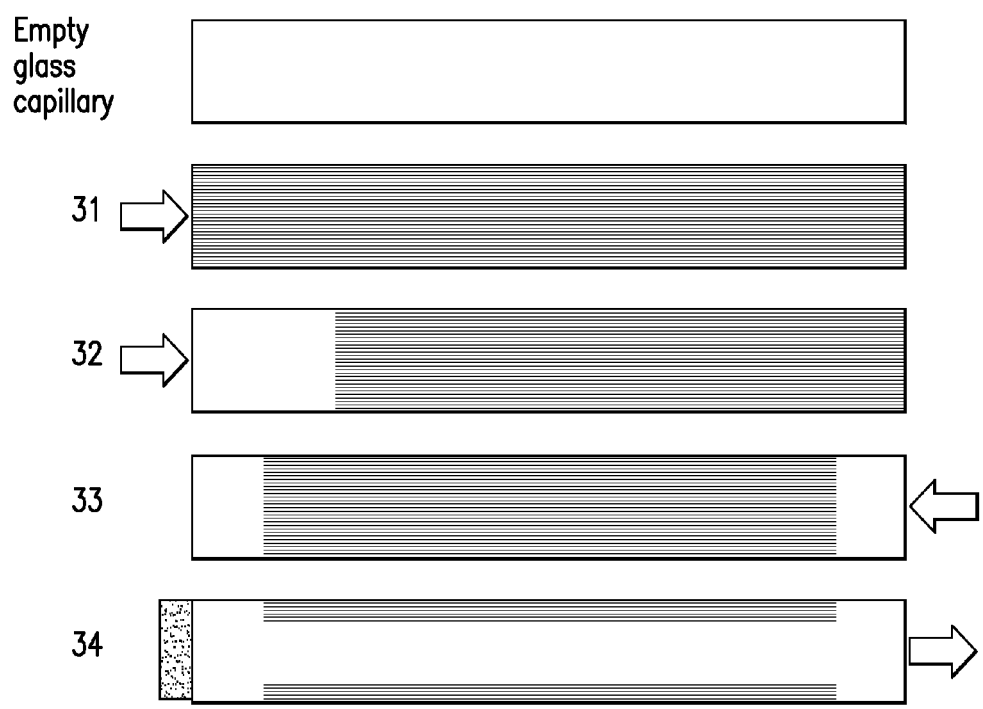
FIG. 3 shows a diagram illustrating a method for preparing a deactivated glass column having particle traps at two end sections in accordance with one embodiment of the invention.

In accordance with some embodiments of the invention, one may make the particle traps first, followed by making the stationary phase. This process typically involves deactivation of the glass column (e.g., coating the column inside with a wax) and making the particle traps. Thus, this method can be practiced in two different ways. In the first approach, one would deactivate the column, and then make the particle traps at both ends of the column. A second approach is to coat the deactivation reagents (e.g., wax) and the reagents for the particle traps (e.g., siloxanes or silicon compounds) in one coating operation. The second approach is easier. Therefore, the following example uses this second approach:

FIG. 3 shows a diagram illustrating the steps involved in this process. First, one starts with an empty column. PLOT columns are typically made of glass capillary tubing that is protected with polymer (e.g., polyimide) coatings on the outside. Fused silica capillary tubings with a polyimide outer coating are commercially available from various sources, for example Polymicro Technologies (Phoenix, Ariz.).

Glass surfaces contain silanol groups (Si—OH), which are reactive and can bind certain analytes or cause tailing of the peaks. Therefore, the glass column needs to be deactivated. Deactivation of a glass column can use any method known in the art. (See, L. Blomberg, J. Chromatogr. 115: 365 (1975)). For example, one may deactivate glass columns using silane reagents (e.g., dimethyldichlorosilane), wax (e.g., Dowex® 20), or polyethyleneglycol (PEG).

First, the glass column is filled with a wax solution (or other deactivation reagent) to deactivate the glass surface (step 31). Deactivation masks the silanol groups on the glass surface. Any reagents that can react with the silanol groups, such as reagents including siloxanes (e.g., hexamethylsilazane, dimethylsiloxane, and methylvinylsiloxane) may be used as deactivation.

After filling with a deactivation solution (e.g., a wax solution), one end of the column is filled with a solution containing a reagent for the particle trap (step 32). The reagent for particle trap may be any chemical that can "catch" the particles that will form the stationary phase. Such reagents, for example, may be silicon compounds or siloxanes. The particle trap solution (e.g., a solution of a siloxane) may be filled from one end (in this example, the left end) to a length (e.g., 6 m) that is twice the intended length (e.g., 3 m) for the final particle trap length.

Next, the other end of the column is similarly filled with the particle trap solution (e.g., a solution of a siloxane) (step 33). The solution is filled from the end at the right side in FIG. 3, which would push some of the silicon solution out of the left end. Thus, each end of the capillary column would have the particle trap solution covering a section of the capillary column to a length (e.g., 3 m) of the intended particle traps.

Figure 4:
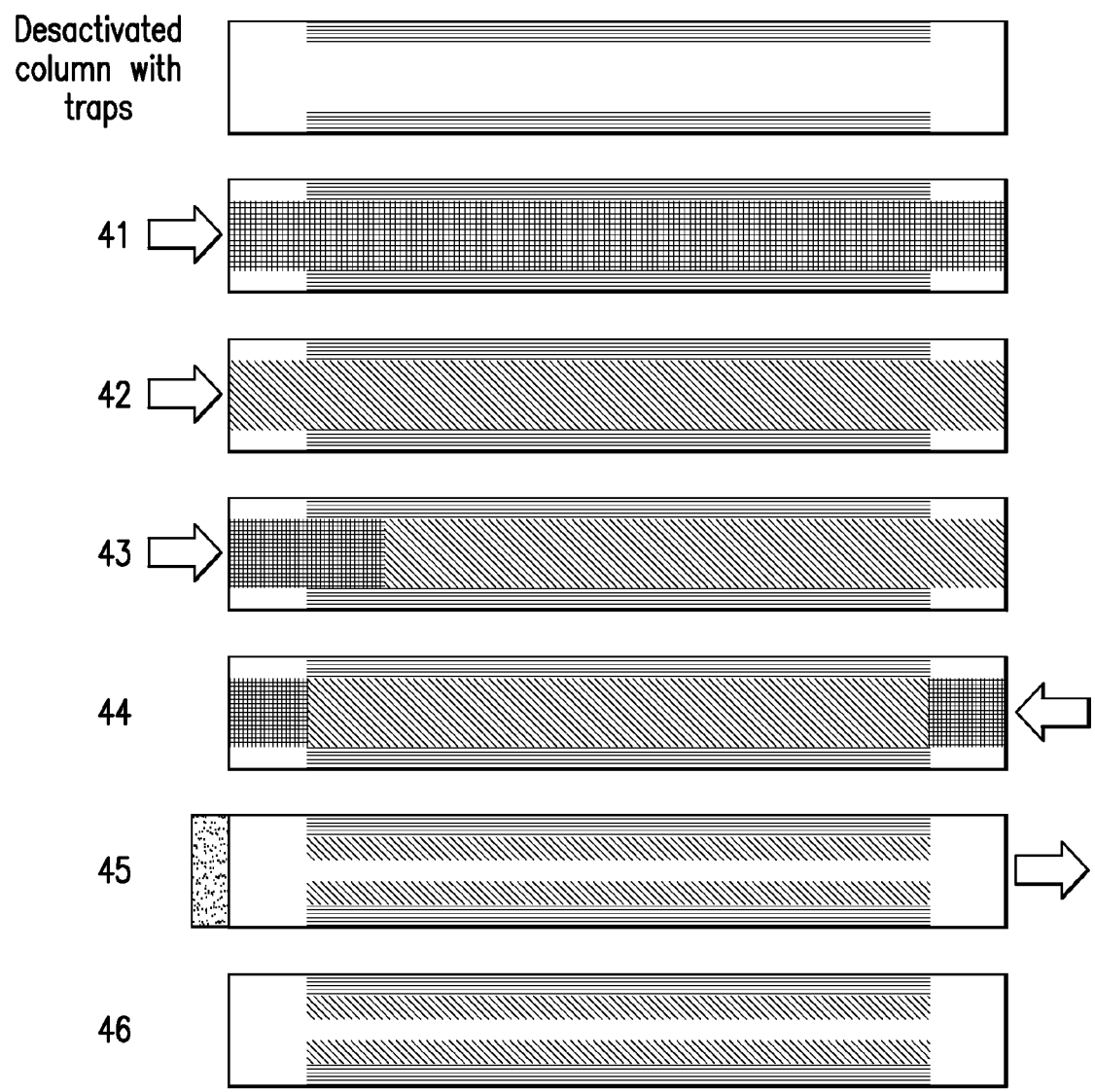
FIG. 4 shows a diagram illustrating a method for making a PLOT column having particle traps in accordance with one embodiment of the invention.

Finally, the solvents are evaporated and the wax is allowed to react with the silanol (i.e., deactivation of Si—OH groups), while the siloxane is allowed to crosslink to form the particle traps (step 34). The deactivated column with particle traps on both ends is now ready for making the stationary phase, as illustrated in the following example:

FIG. 4 shows an example of a procedure for making a PLOT column having integral particle traps on both ends. First, a deactivated column with particle traps at both ends (as obtained from the above procedures illustrated in FIG. 3) is filled with a solvent (step 41). Any solvent that would not react with the particle traps, the deactivated surface, and the PLOT suspension may be used.

Next, a PLOT suspension (i.e., a suspension of styrene-divinylbenzene copolymer) is used to completely fill the capillary column (step 42). A solvent is filled in from one end (the left end shown in FIG. 4) to a length twice the particle trap length (step 43). This pushes the excess PLOT suspension out of the other end (the right end in FIG. 4) of the column.

Next, the PLOT suspension is pushed back from the other end (the right end) by a solvent (or an inert gas, such as nitrogen) to the length of the particle trap (step 44). This step creates a condition in which the PLOT suspension fills the main section of the column, but not the particle trap regions.

The solvent is then evaporated to leave the styrene-divinylbenzene copolymer in the column, and the column is subjected to the coating process (step 45). Finally, after rinsing and conditioning, the column is ready for use (step 46).

The column is subjected to various tests. The introduction of the integral particle traps has no effect on plate count and only a small effect on the selectivity. Thus, the overall performance of the column is not appreciably affected.

There are more possibilities to make integrated particle traps in a column. Some examples are: 1. first make the PLOT phase in the glass or metal capillary, and then make the particle traps on both sides, 2. Make the PLOT phase and the integrated particle traps in one step, 3. Take a standard PLOT column without particle traps, remove the first and last end of the phase from the capillary (e.g. by ultrasonic stripping) and then make the integrated particle traps on both sides, 4. Take a standard PLOT column without particle traps and coat the particle traps direct on top of the PLOT layer. 5. Combinations of the example (FIG. 4), 1, 2, 3 and 4.

The above examples show that integral particle traps indeed function well in preventing particles dislodged from the PLOT columns from reaching detectors. The above examples also show that various methods may be used to prepare these integral particle traps. Even though some methods work better than others, they all produced effective particle traps.

Furthermore, the examples show that the integration of the particle traps with the PLOT columns typically have little impact on the performance of the columns, as measured by the plate numbers, inertness, and retention index.

In table 2 the average chromatographic values are shown of 25 m×0.32 mm PoraBond Q columns with and without integrated particle traps.

TABLE 1

| PoraBOND Q (25 m × 0.32 mm) | | Retentionfactor Ethylacetate | Platenumber Ethylacetate | Asymmetry Ethanol | Retention Index Diethylether | Retention Index Ethylacetate |
|---|---|---|---|---|---|---|
| Columns with two integrated particle traps | Average | 3.78 | 48266 | 1.25 | 482.4 | 553.9 |
| | StDev | 0.24 | 4567 | 0.16 | 0.2 | 0.4 |
| Standard columns | Average | 4.14 | 51411 | 1.40 | 482.9 | 554.7 |
| | StDev | 0.41 | 3734 | 0.23 | 0.1 | 0.2 |

Based on the examples described in table 1, the effects of integral particle traps on the performance of the PLOT columns may be summarized as follows:

Retention index (RI)/selectivity

The materials in particle trap regions have different polarities from the materials used in the stationary phase of a PLOT column. Therefore, the overall selectivity of the column theoretically may be changed. However, the retention index (RI) of the materials for the particle traps is typically lower, as compared with those of the materials for stationary phase in the PLOT columns. Therefore, the actual impact on the overall selectivity of the column by the integration of the particle traps is relatively small. Because the particle traps are typically made about the same length (e.g., 1-3 m), and the PLOT column lengths can vary substantially (e.g., 10-60 m), the overall impact due to the integration of particle traps might be slightly different depending on the PLOT column lengths. For example, there might be a small difference in the impact on RI between a 10 meter column and a 50 or 60 m column.

Figure 5:
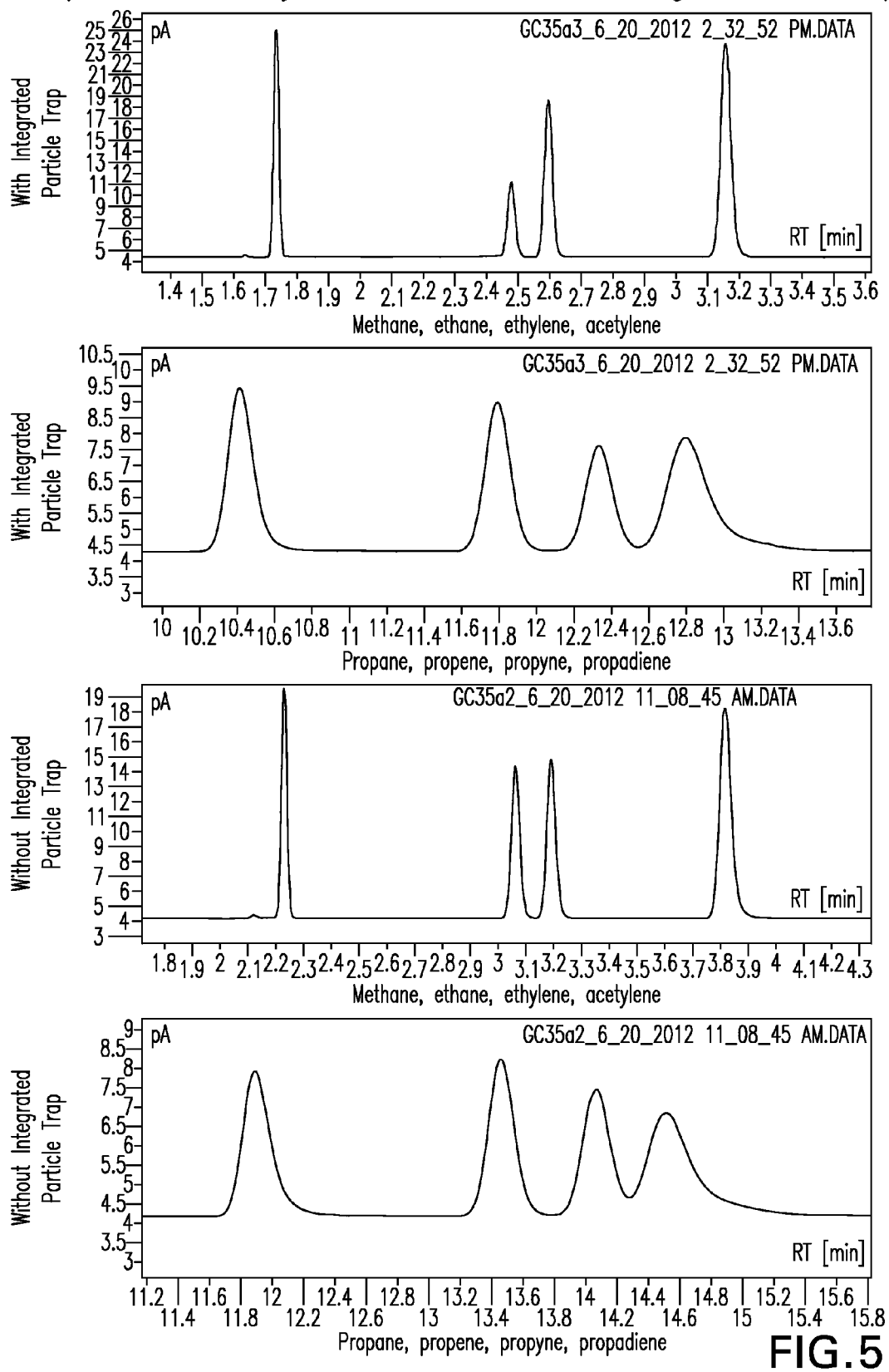
FIG. 5 shows an example of an important application.

An example of an application with and without Integrated Particle Trap is shown in FIG. 5. The retention characteristics are visually the same.

K Value

The Retention Factor (k) is another measure of retention. It is the ratio of the amount of time a solute spends in the stationary phase relative to the amount of time the solute spends in the mobile phase (carrier gas). Based on the examples described herein, it is observed that the k values of PLOT columns may be negatively influenced by the particle traps. Because the particle traps are typically of similar lengths (e.g., 1-3 m) and the PLOT column lengths can vary substantially (e.g., 10-60 m), the impact of the particle traps would be more noticeable with a shorter column. Table 2 shows results, based on theoretical calculations, of possible loss in k of columns having 2.5 m particle traps on each end with varying lengths of the column (stationary phase). Note that it is possible to vary the coating solutions (e.g., different concentrations and/or different compositions) for the particle traps to control the loss in k, so that different lengths of columns may have a similar loss in k.

TABLE 2

| PLOT length (m) | Total particle trap length (m) | Loss in k (%) |
|---|---|---|
| 10 | 5 | 33 |
| 15 | 5 | 25 |
| 25 | 5 | 17 |
| 30 | 5 | 14 |
| 50 | 5 | 9 |
| 60 | 5 | 8 |

To demonstrate the advantages of embodiments of the invention, a PoraPLOT Q column with integral particle traps is compared with a conventional PoraPLOT Q column, under varying pressures and temperatures (i.e., pressure and temperature stress test). The test conditions are as follows:

To test stability, the column temperature is programmed as follows: held at 150° C. for 1 min, ramping at 20° C./min to 250° C., and then held at 250° C. for 1 min. The column is then cooled down. The process is repeated many times during the test. In addition, the PLOT column is operated at a flow rate 3 times higher (e.g., u=1 m/sec) than the normal flow for the column, and flow is turned on and off multiple times (e.g., 10 times) during each temperature cycle. Under these conditions, the forces of expanding and shrinking will take place, which normally cause PLOT columns to release particles, which move through the column and can hit the detector to generate "spikes."

Figure 6:
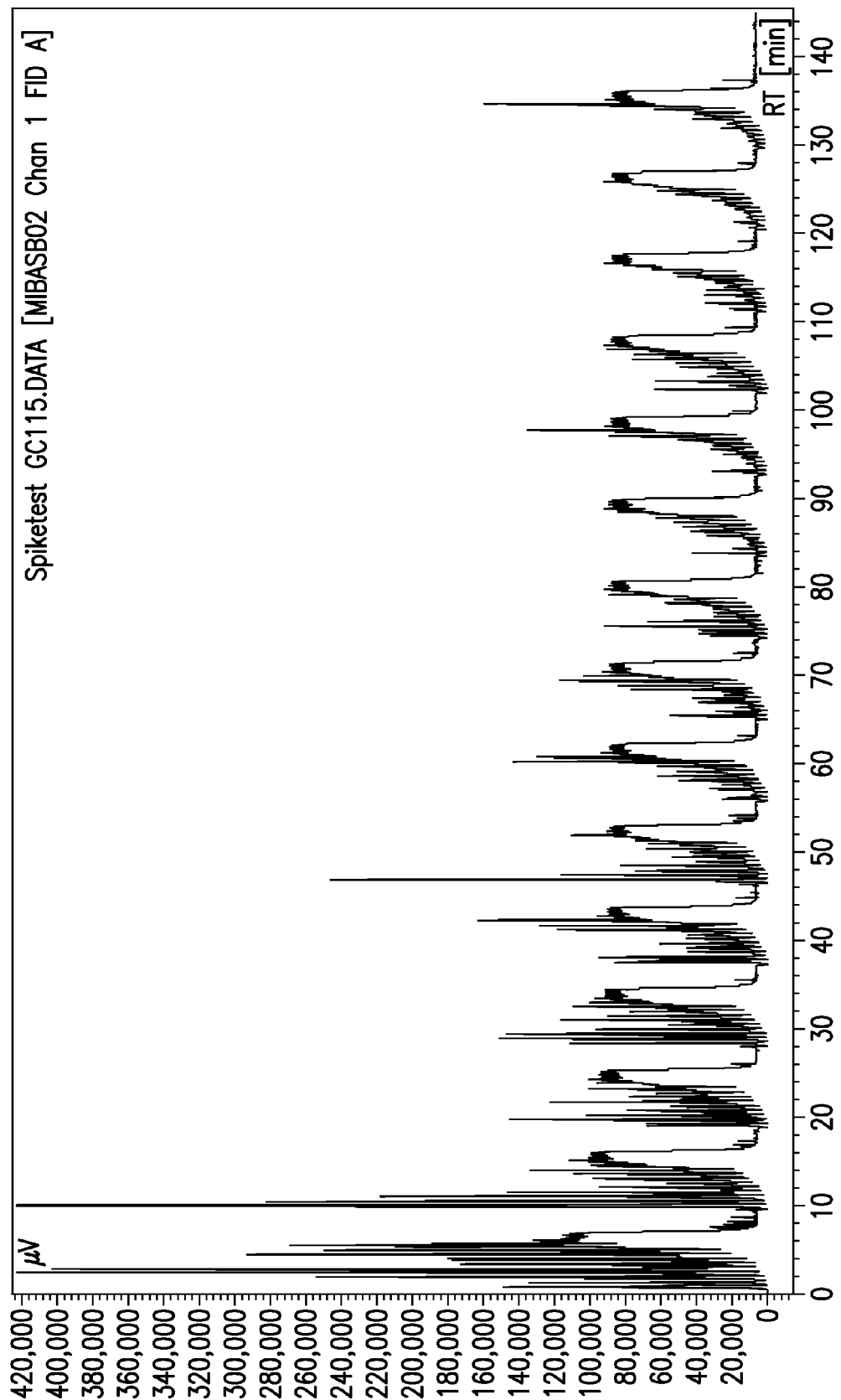
FIG. 6 shows results of pressure and temperature stress tests of a conventional PoraPLOT Q column.

FIG. 6 shows the test results of a conventional 30 m×0.32 mm PoraPLOT Q column.

Figure 7:
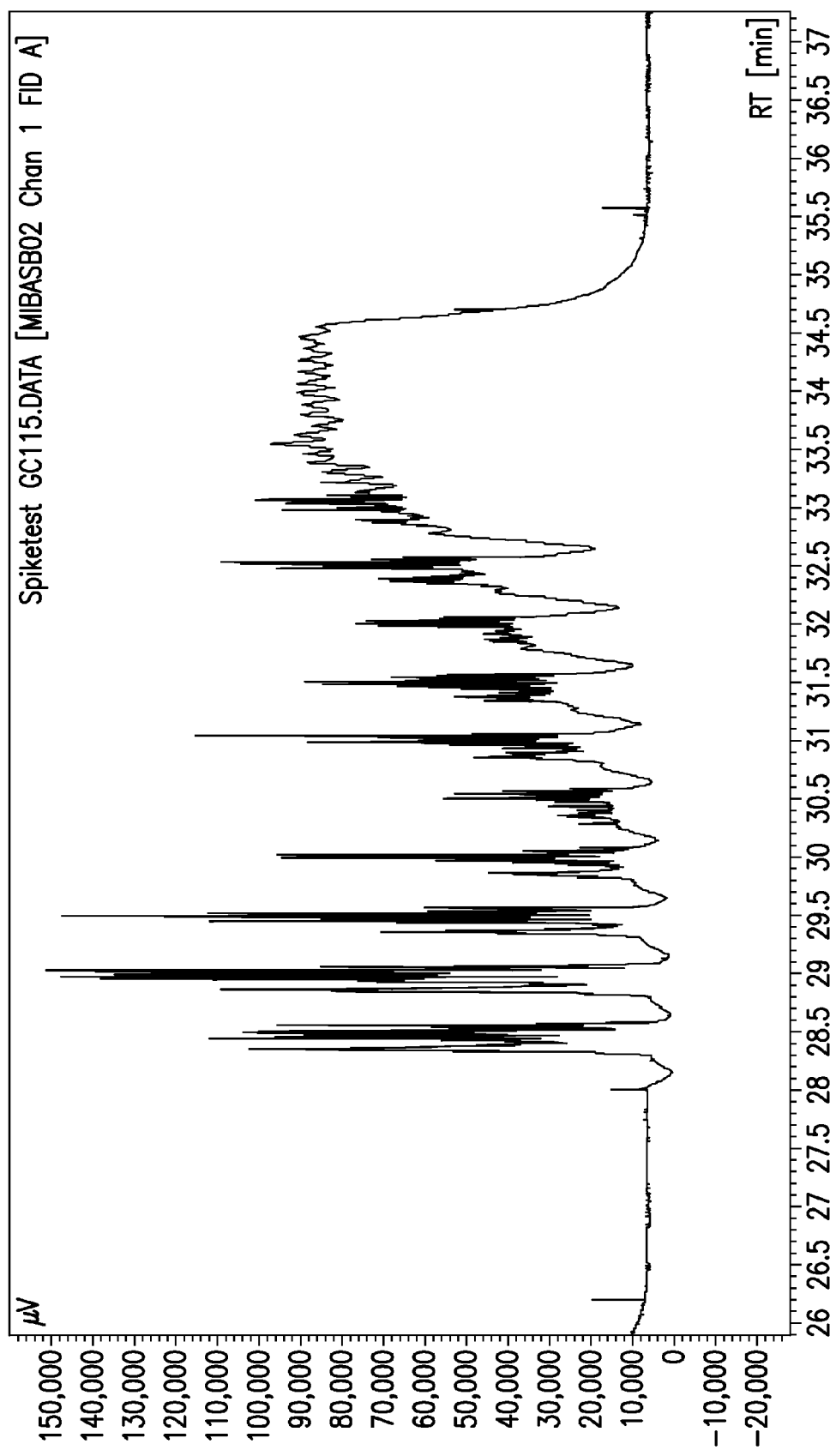
FIG. 7 shows an expanded region of the results shown in FIG. 6.

FIG. 7 shows an expanded region the fourth group of peaks in FIG. 7 (from about 26 min to about 37 min). Many spikes are detected when the flow is turned on and off, indicating that substantially high amounts of particles are dislodged from the PLOT column and reach the detector.

Figure 8:
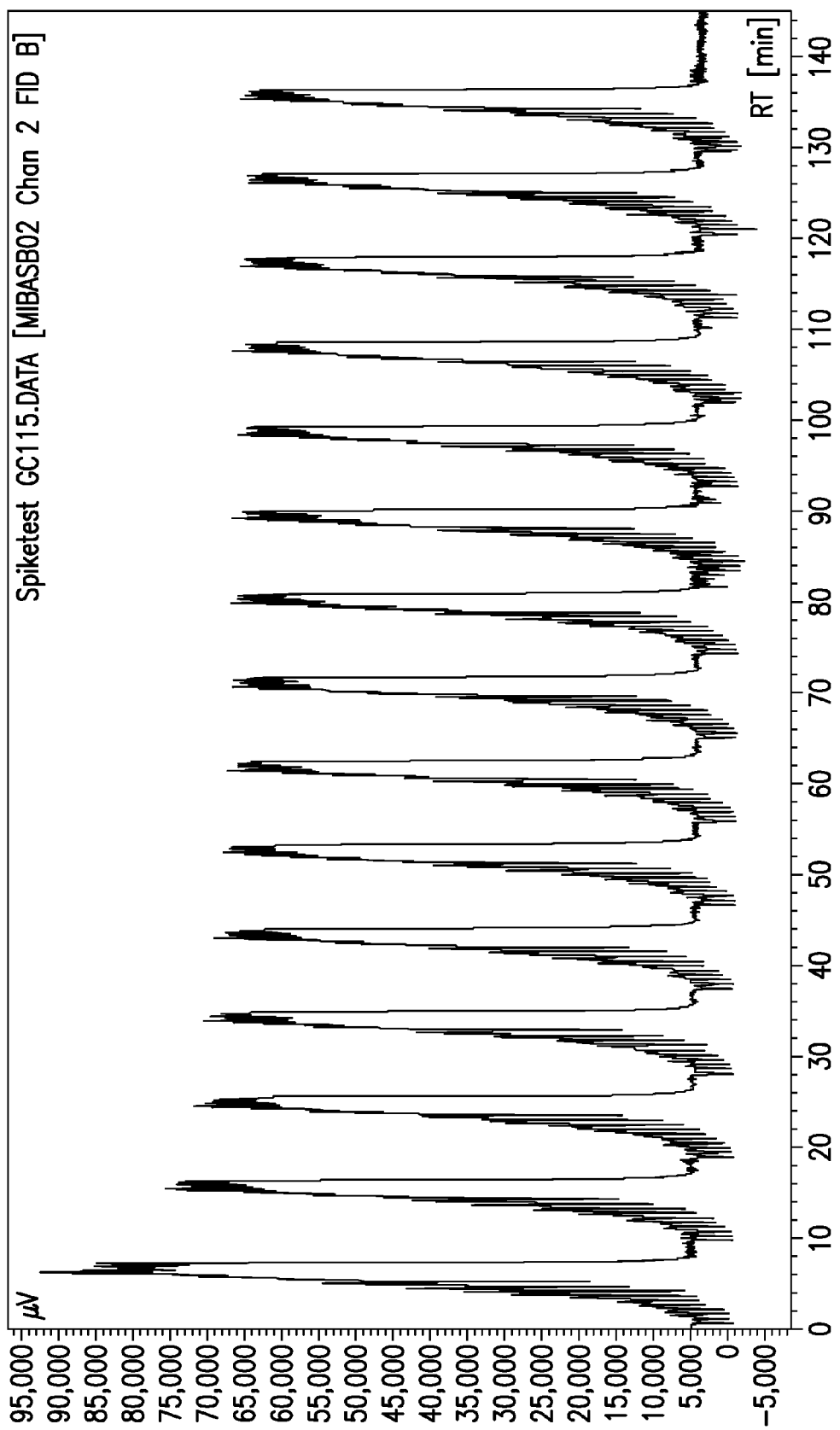
FIG. 8 shows results of pressure and temperature stress tests of a PoraPLOT Q column having particle traps in accordance with one embodiment of the invention.
Figure 9:
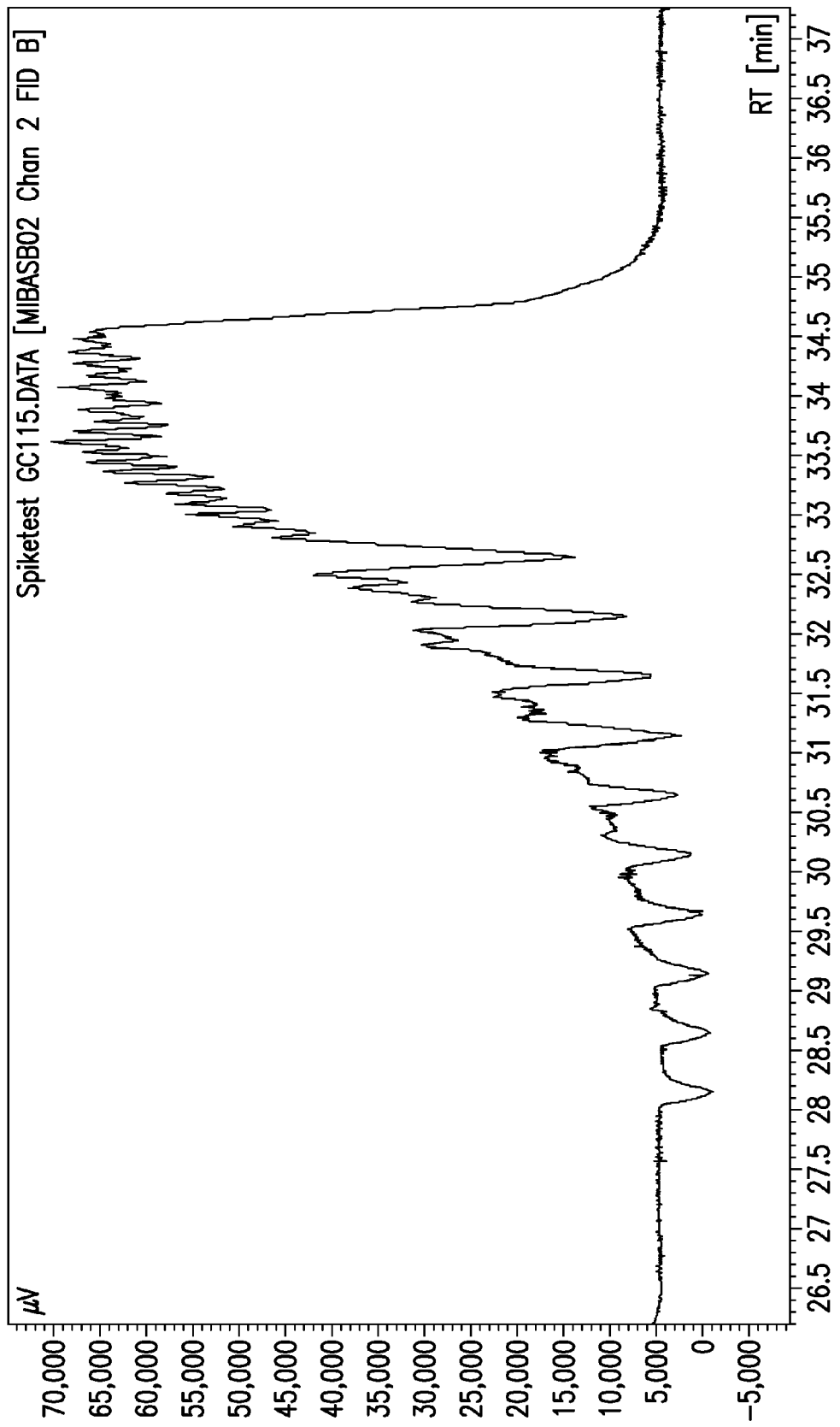
FIG. 9 shows an expanded region of the results shown in FIG. 8.

FIG. 8 shows the test results of a 30 m×0.32 mm PoraPLOT Q column with particle traps according to embodiments of the invention. FIG. 9 shows an expanded region of the fourth group of peaks in FIG. 9 (from about 26 min to about 37 min). In contrast to the results shown in FIG. 7, no spikes are detected when the flow is turned on and off, indicating that no particles reached the detector. Because this column has the same stationary phase as the one tested in FIG. 7, one would expect that the amounts of particles dislodged by the pressure stress would be similar. The fact that no particle reaches the detector attests to the fact that the integral particle traps of the invention are effective.

Furthermore, in the 15 temperature ramping experiments, most signals (except for the first run) are virtually identical among the runs, indicating that the column is quite stable, and that the particle traps continued to perform well during the repeated tests.

Advantages of embodiments of the invention may include one or more of the following. Embodiments of the invention provide PLOT columns with integrated particle traps. With the integral particle traps, no connector is used, and the trap is part of the column. Therefore, these columns will not have the disadvantages of conventional PLOT columns with particle traps connected thereto via connectors. That is, a PLOT column with integral particle traps will not have connectors that may leak and/or clog due to particles being dislodged from the stationary phase in the column. This will prevent the degradation of any valves or detectors, resulting in reduction of the costs in performing the analyses. Furthermore, when used with an integral particle trap on both sides of the column, it is possible to use the column with reversed flow, e.g. in a back flush application. This prevents the contamination of the valve. Furthermore, because the integral particle traps do not appreciably impact the column performance, one should be able to use such columns in existing protocols. In addition, because there are no noisy spikes in the detector signals, the signals would be easier to analyze and the results can be more reliably compared from run to run.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A porous layer open tubular (PLOT) column, comprising:
    a capillary tubing;
    two integrated particle traps disposed inside two end sections of the capillary tubing; and
    a stationary phase comprising a porous layer coated inside a main section of the capillary tubing,
    wherein there is no connector between the capillary tubing and either of the two integrated particle traps.

2. The PLOT column of claim 1, wherein the capillary tubing comprises a glass or metal capillary.

3. The PLOT column of claim 1, wherein each of the integrated particle traps comprises a product of a silicon compound, polysiloxane or wax.

4. The PLOT column of claim 3, wherein each of the integrated particle traps comprises a product of a polysiloxane.

5. The PLOT column of claim 1, wherein the porous layer in the stationary phase comprises a polymer.

6. The PLOT column of claim 5, wherein the polymer is a divinylbenzene polymer or a styrene-divinylbenzene copolymer.

7. A method for preparing a porous layer open tubular (PLOT) column, comprising:
    preparing two integrated particle traps inside two end sections of a capillary tubing; and
    preparing a stationary phase comprising a porous layer coated inside a main section of the capillary,
    wherein there is no connector between the capillary tubing and either of the two integrated particle traps.

8. The method of claim 7, wherein the capillary tubing is a glass or metal capillary.

9. The method of claim 8, further comprising deactivating the glass or metal capillary.

10. The method of claim 9, wherein deactivating the glass or metal capillary is performed prior to preparing two integrated particle traps.

11. The method of claim 7, wherein preparing two integrated particle traps is performed prior to preparing the stationary phase.

12. The method of claim 7, wherein preparing two integrated particle traps is performed after preparing the stationary phase.

13. The method of claim 7, wherein preparing two integrated particle traps and preparing the stationary phase are performed in one step.

14. The method of claim 7, wherein preparing two integrated particle traps is performed by placing the particle traps directly over the stationary phase.

15. The method of claim 7, wherein preparing the stationary phase involves in-situ polymerization.

16. The method of claim 7 comprising all treatments in one step.

17. The method of claim 7, wherein the two integrated particle traps each comprise a product of a polysiloxane.

18. A method for preparing a porous layer open tubular (PLOT) column having two integrated particle traps disposed at the two end sections, comprising:
    stripping a first section of a stationary phase coating from a first end of a PLOT column;
    preparing a first particle trap in the stripped first section;
    stripping a second section of a stationary phase coating from a second end of a PLOT column; and
    preparing a second particle trap in the stripped second section,
wherein there is no connector between the capillary tubing and either of the two integrated particle traps.

* * * * *